US007189890B2

(12) United States Patent
Ozawa et al.

(10) Patent No.: US 7,189,890 B2
(45) Date of Patent: Mar. 13, 2007

(54) GENE RELATED TO REGENERATION ABILITY OF PLANTS AND USES THEREOF

(75) Inventors: Kenjirou Ozawa, Tsukuba (JP); Hiroyuki Kawahigashi, Tsukuba (JP); Toshiaki Kayano, Tsukuba (JP); Yasunobu Ohkawa, Tuskuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 181 days.

(21) Appl. No.: 10/264,341

(22) Filed: Oct. 4, 2002

(65) Prior Publication Data

US 2003/0188342 A1 Oct. 2, 2003

(30) Foreign Application Priority Data

Apr. 2, 2002 (JP) ............................. 2002-100358

(51) Int. Cl.
  C12N 15/29 (2006.01)
  C12N 15/82 (2006.01)
  C12N 5/04 (2006.01)
  A01H 5/00 (2006.01)
(52) U.S. Cl. ...................... 800/278; 800/298; 800/290; 536/23.6; 435/320.1; 435/419
(58) Field of Classification Search ............... 536/23.1, 536/23.6; 435/320.1, 468; 800/298, 278
See application file for complete search history.

(56) References Cited

FOREIGN PATENT DOCUMENTS

JP 3-7599 A 1/1991

OTHER PUBLICATIONS

Fourgoux-Nicol et al (1999, Plant Molecular Biology 40:857-872).*
Bowie et al, Science 247:1306-1310, 1990.*
McConnell et al, Nature 411 (6838):709-713, 2001.*
Alexander et al (1994 Planta 192(4):519-525).*
Kawahigashi, H. et al., "RFLP analysis of Koshihikari isogenic lines with high ability of regeneration," *Breeding Science 3*, Suppl. 2, p. 10, Japanese Society of Breeding (Oct. 7, 2001).
Ozawa, K. et al., "Cloning and analysis of the genes correlated with the regeneration ability using the differential display in *Oryza sativa*," *Breeding Science 3*, Suppl. 2, p. 131, Japanese Society of Breeding (Oct. 7, 2001).
English translation of Kawahigashi, H. et al., "RFLP analysis of Koshihikari isogenic lines with high ability of regeneration," *Breeding Science 3*, Suppl. 2, p. 10, Japanese Society of Breeding (Oct. 7, 2001).
English translation of Ozawa, K. et al., "Cloning and analysis of the genes correlated with the regeneration ability using the differential display in *Oryza sativa*," *Breeding Science 3*, Suppl. 2, p. 131, Japanese Society of Breeding (Oct. 7, 2001).
English language abstract of JP-7599 A, cited on Form PTO/SB/08A as document AL1.
Kwon, Y.-S., et al., "Marker-assisted Selection for Identification of Plant Regeneration Ability of Seed-derived Calli in Rice (*Oryza sativa* L.)," *Mol. Cells* 12:103-106, Korean Society for Molecular Biology (Aug. 2001).
Toshinori, A., "Genetic control of Dedifferentiation/Redifferentiation of rice," *Idenshi Igaku* 5:32-38, Ine Idengaku no Saikochiku (1995).
Unverified English translation of Toshinori, A., "Genetic control of Dedifferentiation/Redifferentiation of rice," *Idenshi Igaku* 5:32-38, Ine Idengaku no Saikochiku (1995), document AR3.
Ozawa et al., "Genetic analyses of the redifferentiation ability of rice and development of breeding materials for high redifferentiation ability," *Nougyoseibutsushigenkenkyujo Shuyo-na-kenkyu-seika*, pp. 82-83, National Institute of Agrobiological Sciences (May 2002).
Unverified English translation of Ozawa et al., "Genetic analyses of the redifferentiation ability of rice and development of breeding materials for high redifferentiation ability," *Nougyoseibutsushigenkenkyujo Shuyo-na-kenkyu-seika*, pp. 82-83, National Institute of Agrobiological Sciences (May 2002).
Yoshida, K.T., et al., "cDNA Cloning of Regeneration-Specific Genes in Rice by Differential Screening of Randomly Amplified cDNAa Using RAPD Primers," *Plant Cell Physiol.* 35:1003-1009, Oxford University Press (1994).
Office Action for Japanese Patent Application No. 2002-314937, Japanese Patent Office.
Partial English Translation of Office Action for Japanese Patent Application No. 2002-314937.

* cited by examiner

*Primary Examiner*—Stuart F. Baum
(74) *Attorney, Agent, or Firm*—Sterne, Kessler, Goldstein & Fox P.L.L.C.

(57) ABSTRACT

The objective is to isolate and identify a gene relating to the regeneration ability of a plant, and to provide the gene and methods of use thereof. Isogenic lines to which culture characteristics of Konansou was introduced were produced by backcrossing. Culture cells were induced from this isogenic line and its parent variety. After confirming the regeneration ability of culture cells cultured for 3 to 6 months, isolation of a gene expressed in culture cells derived from Konansou and an isogenic line having a high regeneration ability, but not expressed in culture cells derived from Sasanishiki and Koshihikari was conducted using the differential display method. As a result, a regeneration-related gene was successfully cloned.

14 Claims, 10 Drawing Sheets

SEQUENCE LISTING

```
<160> NUMBER OF SEQ ID NOS: 2

<210> SEQ ID NO 1
<211> LENGTH: 1416
<212> TYPE: DNA
<213> ORGANISM: Oryza sativa
<220> FEATURE:
<221> NAME/KEY: CDS
<222> LOCATION: (243)..(1145)

<400> SEQUENCE: 1
ggaccaccca cctcgccgcg ccacgtacgc cgcatcgcat gcgcgcgctc tccctcgcca      60
gagcaagtag cccgccgcct cttcttcttc acctccgacg agcccttgca cccgcgtcgt     120
cgtcttctcc ggcgccggtg ctgttgctgc gtcctgcggt ttcttgttct tctttgtttg     180
ttagcgacag ggcggcggcg gcggcggcgg ctcgccggag cagcggcagc agcaggagaa     240 gc atg gcg tcg cag cag ttc ccg ccg cag aag cag gag acg cag ccg        287
   Met Ala Ser Gln Gln Phe Pro Pro Gln Lys Gln Glu Thr Gln Pro
   1               5                  10                  15 ggg aag gag cac gcc atg gat ccc cgc ccc gag gcc atc atc cag agc        335
Gly Lys Glu His Ala Met Asp Pro Arg Pro Glu Ala Ile Ile Gln Ser
                20                  25                  30 tac aag cca gcc aac aag ctg aag gac gag gtg gcg atc gtg acc ggc        383
Tyr Lys Pro Ala Asn Lys Leu Lys Asp Glu Val Ala Ile Val Thr Gly
            35                  40                  45 ggc gac tcc ggc atc ggg cgg gcg gtg tgc ctg tgc ttc gcg ctg gag        431
Gly Asp Ser Gly Ile Gly Arg Ala Val Cys Leu Cys Phe Ala Leu Glu
        50                  55                  60 ggc gcg acg gtg gcg ttc acg tac gtg aag ggg cag gag gag aag gac        479
Gly Ala Thr Val Ala Phe Thr Tyr Val Lys Gly Gln Glu Glu Lys Asp
    65                  70                  75 gcg gag gag acg ctc cgc gcg ctg cgc gac atc agg gcg cgc acc ggc        527
Ala Glu Glu Thr Leu Arg Ala Leu Arg Asp Ile Arg Ala Arg Thr Gly
80                  85                  90                  95 gcc aag gac ccc atg gcg atc ccc gcc gac ctc ggg tac gac gac aac        575
```

| | | |
|---|---|---|
| tgc cgc aag gtg gtc gac gag gtc gcc ggc gcg tac ggc ggc gcc atc<br>Cys Arg Lys Val Val Asp Glu Val Ala Gly Ala Tyr Gly Gly Ala Ile<br>115                      120                      125 | 623 |
| gac atc ctc gtc aac aac gcc gcc gag cag tac gag cgc ccc tcc atc<br>Asp Ile Leu Val Asn Asn Ala Ala Glu Gln Tyr Glu Arg Pro Ser Ile<br>130                      135                      140 | 671 |
| acc gac atc acc gag gac gac ctg gaa cgc gtg ttc cgc acc aac atc<br>Thr Asp Ile Thr Glu Asp Asp Leu Glu Arg Val Phe Arg Thr Asn Ile<br>145                      150                      155 | 719 |
| ttc tcc tac ttc ttc atg tcg aag cac gcc gtg aag cgg atg cgc gat<br>Phe Ser Tyr Phe Phe Met Ser Lys His Ala Val Lys Arg Met Arg Asp<br>160                  165                      170                  175 | 767 |
| cgc cgc ggc ggc gcc ggc gcc ggc ggg tgc agc atc atc aac acg tcg<br>Arg Arg Gly Gly Ala Gly Ala Gly Gly Cys Ser Ile Ile Asn Thr Ser<br>                  180                      185                      190 | 815 |
| tcg atc aac gcg tac aag ggg aac aag acg ctg ctg gac tac acg gcg<br>Ser Ile Asn Ala Tyr Lys Gly Asn Lys Thr Leu Leu Asp Tyr Thr Ala<br>                  195                      200                      205 | 863 |
| acc aag ggc gcc atc gtg gcg ttc acg agg gcg ctg gcg ctg cag ctg<br>Thr Lys Gly Ala Ile Val Ala Phe Thr Arg Ala Leu Ala Leu Gln Leu<br>210                      215                      220 | 911 |
| gcg gag gag ggg atc cgg gtg aac ggc gtc gcg ccg ggg ccg atc tgg<br>Ala Glu Glu Gly Ile Arg Val Asn Gly Val Ala Pro Gly Pro Ile Trp<br>225                      230                      235 | 959 |
| acg ccg ctg atc ccg gcg tcg ttc gcg gag gag aag gtg agg cag ttc<br>Thr Pro Leu Ile Pro Ala Ser Phe Ala Glu Glu Lys Val Arg Gln Phe<br>240                      245                      250                  255 | 1007 |
| ggc tcc cag gtg ccc atg ggc cgc gcc ggc cag ccg tcg gag gtg gcg<br>Gly Ser Gln Val Pro Met Gly Arg Ala Gly Gln Pro Ser Glu Val Ala<br>                  260                      265                      270 | 1055 |
| ccc agc ttc gtc ttc ctc gcc agc gac gac gcc tcc tac atg tcc ggc<br>Pro Ser Phe Val Phe Leu Ala Ser Asp Asp Ala Ser Tyr Met Ser Gly<br>                  275                      280                      285 | 1103 |
| cag atg ctg cac gtc aac ggc ggc gtc atc gtc aat ggc tagttttca<br>Gln Met Leu His Val Asn Gly Gly Val Ile Val Asn Gly<br>290                      295                      300 | 1152 |
| cttgtcccat atcgccgccg gcgggcgagc tcgccgtcgc cggccgccgt gtctgtcttg | 1212 |
| gcttttgctg tgggcatgtg cccacgtgtt tgcagtgcga gtccaccaca tgtcagtcag | 1272 |
| tagtagcttg tgatcctgtg atactgtgat gattagagtt gcagttgttg tctgtgtcct | 1332 |
| aagcttgcaa ctcaatctgc aaggaagaag atgaataaaa acgtcccatc tcatcactaa | 1392 |
| aaaaaaaaaa aaaaaaaaaa aaaa | 1416 |

<210> SEQ ID NO 2
<211> LENGTH: 300
<212> TYPE: PRT
<213> ORGANISM: Oryza sativa

<400> SEQUENCE: 2

Met Ala Ser Gln Gln Phe Pro Pro Gln Lys Gln Glu Thr Gln Pro Gly
 1               5                  10                  15

Lys Glu His Ala Met Asp Pro Arg Pro Glu Ala Ile Ile Gln Ser Tyr
             20                  25                  30

Lys Pro Ala Asn Lys Leu Lys Asp Glu Val Ala Ile Val Thr Gly Gly
         35                  40                  45

Asp Ser Gly Ile Gly Arg Ala Val Cys Leu Cys Phe Ala Leu Glu Gly

-continued

```
                      50                  55                  60
Ala Thr Val Ala Phe Thr Tyr Val Lys Gly Gln Glu Glu Lys Asp Ala
 65                      70                  75                  80

Glu Glu Thr Leu Arg Ala Leu Arg Asp Ile Arg Ala Arg Thr Gly Ala
                     85                  90                  95

Lys Asp Pro Met Ala Ile Pro Ala Asp Leu Gly Tyr Asp Asp Asn Cys
                    100                 105                 110

Arg Lys Val Val Asp Glu Val Ala Gly Ala Tyr Gly Gly Ala Ile Asp
                    115                 120                 125

Ile Leu Val Asn Asn Ala Ala Glu Gln Tyr Glu Arg Pro Ser Ile Thr
130                     135                 140

Asp Ile Thr Glu Asp Asp Leu Glu Arg Val Phe Arg Thr Asn Ile Phe
145                     150                 155                 160

Ser Tyr Phe Phe Met Ser Lys His Ala Val Lys Arg Met Arg Asp Arg
                    165                 170                 175

Arg Gly Gly Ala Gly Ala Gly Gly Cys Ser Ile Ile Asn Thr Ser Ser
                    180                 185                 190

Ile Asn Ala Tyr Lys Gly Asn Lys Thr Leu Leu Asp Tyr Thr Ala Thr
                    195                 200                 205

Lys Gly Ala Ile Val Ala Phe Thr Arg Ala Leu Ala Leu Gln Leu Ala
                    210                 215                 220

Glu Glu Gly Ile Arg Val Asn Gly Val Ala Pro Gly Pro Ile Trp Thr
225                     230                 235                 240

Pro Leu Ile Pro Ala Ser Phe Ala Glu Glu Lys Val Arg Gln Phe Gly
                    245                 250                 255

Ser Gln Val Pro Met Gly Arg Ala Gly Gln Pro Ser Glu Val Ala Pro
                    260                 265                 270

Ser Phe Val Phe Leu Ala Ser Asp Asp Ala Ser Tyr Met Ser Gly Gln
                    275                 280                 285

Met Leu His Val Asn Gly Gly Val Ile Val Asn Gly
                    290                 295                 300
```

GENE RELATED TO REGENERATION ABILITY OF PLANTS AND USES THEREOF

BACKGROUND OF THE INVENTION

1. Field of the Invention

The present invention relates to a gene involved in the regeneration ability of plants and its uses.

2. Background Art

The establishment of a culture cell-regenerating system is important, as it is a key technology used in plant transformation systems. However, such an establishment of a system for inducing and regenerating culture cells is dependent on plant species, and no general method has been found so far. Moreover, even among the same plant species, there are significant differences between varieties, and therefore, trial-and-error and much effort are required to establish a culture system. Specifically, plants of Poaceae are reported to have quite different regeneration abilities among varieties. In addition, in spite of the economical importance, rice varieties such as Koshihikari have poor culture characteristics and many varieties are known for being difficult to establish a culture cell-regenerating system with. Furthermore, the regenerating ability tends to drop rapidly in cultured cells, which is another big problem.

SUMMARY OF THE INVENTION

This need in the art led to the present invention, the objective of which is to isolate and identify a gene involved in the regeneration ability of plants and to provide the gene and methods to utilize the gene. More specifically, the objective of the present invention is to provide a gene involved in the regeneration ability of plants, a plant transformant having the gene, a method of producing the plant transformant, a method of determining the regeneration ability of a plant using the gene as a marker, and a reagent to be used in the method.

The present inventors produced isogenic lines of the *japonica* variety, Sasanishiki (B6F3) and Koshihikari (B4F3), introduced with the culture characteristics (the induced culture cell proliferate fast and has a high regeneration ability) of Konansou, an indica variety, by backcrossing. Culture cells were induced from the produced isogenic line and the parent cell. After a 3 to 6 month culture, the regeneration ability of the culture cells was confirmed, and genes expressed in culture cells derived from Konansou and the isogenic line, which have a high regeneration ability, but not in culture cells derived from Sasanishiki and Koshihikari, were isolated by the differential display method. As a result, the present inventors succeeded in cloning a gene involved in regeneration, named the 22A gene. Further, similar to results obtained by the differential display method, Northern hybridization revealed that the 22A gene expression could be detected not in Koshihikari and Sasanishiki, but only in Konansou and the isogenic lines of Koshihikari and Sasanishiki that have a high regeneration ability. Furthermore, gene expression could not be observed in the isogenic lines of Koshihikari with a reduced regeneration ability comparable to Koshihikari.

To confirm the relevance of the 22A gene in the regeneration of Konansou, two Koshihikari isogenic lines B4F3, which have a high regeneration ability, were backcrossed with Koshihikari to obtain the generation B5F3. The regeneration ability of B5F3 was confirmed, and the sample was subjected to Northern hybridization. As a result, 22A gene expression was confirmed in the isogenic lines of Koshihikari that have a high regeneration ability, but not in the isogenic lines with a reduced regeneration ability.

Furthermore, Northern hybridization analysis was conducted to examine 22A gene expression in 13 other varieties of rice. The regeneration ability hardly reduced with passage in four varieties (i.e., Konansou, NepVai, Kele, and Panbira) wherein the 22A gene expression was high compared to other varieties. On the other hand, no 22A gene expression could be detected in Koshihikari, IR8, and Konansen, which have a low regeneration rate from the beginning of the culture. In some of the varieties, the gene was expressed at the beginning of the culture, but almost disappeared after a 4-month culture. Further, the regeneration rate decreased in accordance with the disappearance of the gene in these varieties.

According to the results above, the 22A gene was demonstrated to be the gene involved in regeneration. Moreover, it was revealed that the gene could be used as a marker to select plant cells with a high regeneration ability, and by introducing the gene into plant cells, the regeneration ability can be conferred to plant cells.

The present invention relates to a gene involved in the regeneration ability of plants and uses thereof. More specifically, the present invention provides the following:

(1) a DNA related to the regeneration ability of a plant, wherein the DNA is selected from the group consisting of:

(a) a DNA encoding a protein comprising the amino acid sequence of SEQ ID NO: 2;

(b) a DNA comprising a coding region of the nucleotide sequence of SEQ ID NO: 1;

(c) a DNA encoding a protein comprising the amino acid sequence of SEQ ID NO: 2 in which one or more amino acids have been substituted, deleted, inserted and/or added; and (d) a DNA hybridizing under stringent conditions to the DNA comprising the nucleotide sequence of SEQ ID NO: 1;

(2) a DNA encoding a partial peptide of the protein comprising the amino acid sequence of SEQ ID NO: 2;

(3) a vector into which the DNA according to (1) or (2) has been introduced;

(4) a transformed plant cell harboring the DNA according to (1) or 2, or the vector according to (3);

(5) a plant transformant comprising the transformed plant cell according to (4);

(6) a plant transformant which is a progeny or clone of the plant transformant according to (5);

(7) a propagation material of the plant transformant according to (5) or (6);

(8) a method for producing the plant transformant according to (5), wherein the method comprises the following steps of:

(a) introducing the DNA according to (1) or (2) or the vector according to (3) into a plant cell; and (b) regenerating a plant from said plant cell;

(9) a method for determining the presence of the regeneration ability in a plant cell, wherein the method comprises the following steps of:

(a) detecting the expression level of the DNA according to (1) in a plant cell; and (b) comparing the expression level of the DNA according to (1) detected in step (a) with the result obtained for a control cell, wherein the plant cell is determined to have a high regeneration ability when the expression level of the DNA according to (1) detected in step (a) is higher than that obtained for the control cell; and (10) a reagent for detecting the presence of the regeneration ability in a plant cell, wherein then reagent comprises an oligonucleotide that hybridizes with the DNA according to (1) and comprises at least 15 nucleotides.

DETAILED DESCRIPTION OF THE INVENTION

The present invention provides DNAs related to regeneration of plants. The nucleotide sequence of the cDNA of the 22A gene isolated in the present invention is set forth in SEQ ID NO: 1, and the amino acid sequence of the protein encoded by the cDNA is set forth in SEQ ID NO: 2.

The DNAs according to the present invention may be derived from any kind of plant including, but not limited to, rice, maize, barley, and wheat.

Herein, the term "regeneration" refers to the ability of a plant cell (callus, etc.) to reproduce the original plant. Until the present invention, whether a plant cell has the ability to regenerate or not was just determined visually (by whether a shoot is formed from a plant cell such as a callus planted on a regeneration medium). The present invention provides methods for determining the regeneration ability of a plant cell by using a DNA according to the present invention or the protein encoded by a DNA according to the present invention as a marker.

The DNA of the present invention involved in the regeneration ability includes genomic DNA, cDNA and chemically synthesized DNA. Genomic DNA and cDNA can be prepared by a conventional method known to one skilled in the art. Genomic DNA can be prepared, for example, by extracting genomic DNA from a rice variety having a DNA according to the present invention, constructing a genomic library (examples of vectors that may be used are plasmids, phages, cosmids, BACs, PACs, and such), plating it, and performing colony hybridization or plaque hybridization using a probe that is prepared based on a DNA according to the present invention (for example, SEQ ID NO: 1). In addition, genomic DNA can also be prepared by constructing a primer specific to a DNA according to the present invention (for example, SEQ ID NO: 1), and then using it to perform PCR. cDNA can be prepared, for example, by synthesizing cDNA based on mRNA extracted from a rice variety having a DNA according to the present invention, inserting this into a vector such as λZAP to construct a cDNA library, plating it, then performing colony hybridization or plaque hybridization in a manner similar to that mentioned above, or by performing PCR.

The present invention includes a DNA encoding a protein that is structurally similar to the protein comprising the amino acid sequence of SEQ ID NO: 2, and is involved with regeneration ability.

Whether or not a certain DNA encodes a protein involved in the regeneration ability can be verified by inducing culture cells from plants introduced with a test DNA, and then observing whether or not the culture cells regenerate. For example, if a shoot is formed from the culture cell, about three weeks after planting the culture cell on a regeneration medium, the test DNA is judged to encode a protein involved in the regeneration ability.

Such DNAs include, for example, mutants, derivatives, alleles, variants, and homologs encoding a protein comprising an amino acid sequence in which one or more amino acids of the amino acid sequence of SEQ ID NO: 2 have been replaced, deleted, added and/or inserted. A method well known to one skilled in the art for preparing DNA that encodes a protein with a modified amino acid sequence is, for example, site-directed mutagenesis (Kramer, W. & Fritz, H. -J.: Methods Enzymol. 154: 350, 1987). In addition, even in the natural world, a mutation may occur in the amino acid sequence of an encoded protein due to a mutation of the nucleotide sequence. Even if a DNA encodes a protein having an amino acid sequence in which one or more amino acids of the amino acid sequence of SEQ ID NO: 2 have been replaced, deleted, added, and/or inserted by a naturally occurring mutation, it is included in the DNA according to the present invention as long as it encodes a protein functionally equivalent to the natural protein (SEQ ID NO: 2). There are also cases where a mutation of the nucleotide sequence does not result in a mutation of the amino acid sequence (degenerate mutation). Such degenerate mutants are also included in the DNA of this invention.

Examples of methods well known to one skilled in the art for preparing DNA encoding a protein that is functionally equivalent to a protein comprising the amino acid sequence of SEQ ID NO: 2, are methods utilizing hybridization techniques (Southern E. M., J. Mol. Biol. 98: 503, 1975) and polymerase chain reaction (PCR) techniques (Saiki, R. K., et al, Science 230: 1350, 1985; Saiki, R. K., et al, Science 239: 487, 1988). That is, isolating DNA that is highly homologous to the 22A gene from rice and other plants by using the nucleotide sequence of the 22A gene (SEQ ID NO: 1) or its portion as a probe, or by using an oligonucleotide that hybridizes specifically to the 22A gene (SEQ ID NO: 1) as a primer may be routinely performed by one skilled in the art. Thus, DNAs encoding proteins functionally equivalent to a protein comprising the amino acid sequence of SEQ ID NO: 2, which may be isolated by hybridization techniques or PCR techniques, are included in the DNA according to the present invention.

Preferably, hybridization is performed under stringent conditions to isolate such DNA. Stringent hybridization conditions according to the present invention refer to 6 M urea, 0.4% SDS, and 0.5×SSC, or a hybridization condition with a stringency equivalent to these conditions. With conditions of higher stringency, for example, under conditions of 6 M urea, 0.4% SDS, and 0.1×SSC, isolation of DNA with higher homology can be expected. High homology refers to a sequence identity of at least 50% or more, preferably 70% or more, more preferably 90% or more, and most preferably 95% or more in the entire amino acid sequence.

The identity of amino acid sequences and nucleotide sequences can be determined using the BLAST algorithm according to Karlin and Altschul (Proc. Natl. Acad. Sci. USA 87:2264–2268, 1990; Karlin, S. & Altschul, S. F., Proc. Natl. Acad. Sci. USA 90: 5873, 1993). Programs called BLASTN and BLASTX have been developed based on the algorithm of BLAST (Altschul, S. F., et al, J. Mol. Biol. 215: 403, 1990). When a nucleotide sequence analysis is performed using BLSTN, the parameters are set at score=100, and wordlength=12, or example. Also, when an amino acid sequence is analyzed using BLASTX, the parameters are set at score=50, and wordlength=3, for example. When BLAST or Gapped BLAST program is used, default parameters for each of the programs are used. Specific techniques for these analysis methods are known (see the website of NIH's National Center for Biotechnology Information).

In addition, the present invention provides a DNA encoding a partial peptide of a protein comprising the amino acid sequence of SEQ ID NO: 2.

In the present invention, the DNA mentioned above, or a protein encoded by the above-mentioned DNA may be a marker for determining whether or not a plant cell has the regeneration ability. Furthermore, the DNA mentioned above can be used for introducing the property of high regeneration ability into plant cells.

Furthermore, the present invention includes a vector in to which the DNA according to the present invention has been inserted, a transformed plant cell harboring the DNA according to the present invention or the vector, a plant possessing these cells, progenies and clones of the plant, as well as propagation material of the plant, its progenies, and clones.

To construct a plant transformant of the present invention, the DNA according to the present invention or the vector in which the DNA according to the present invention has been inserted are introduced into plant cells, and the obtained transformed plant cells are regenerated.

In the present invention, there are no limitations on the vector used for transformation of a plant cell as long as it can express the inserted gene within the cell. For example, a vector having a promoter for constantly expressing genes in plant cells (for example, the 35S promoter of the cauliflower mosaic virus), and a vector having a promoter that is inductively activated by an external stimulus may be used.

In addition, "plant cells" of the present invention includes plant cells of various morphologies, for example, culture cells, protoplasts, sections of leaves, and calli. Furthermore, there are no particular limitations on the plants from which the plant cells are derived.

For introducing a vector into a plant cell, various methods such as the polyethylene glycol method, electroporation method, an Agrobacterium-mediated method, and particle gun method that are known to those skilled in the art can be used. Regeneration of a plant from a transformed plant cell can be performed by methods known to those skilled in the art according to the type of plant cell used (Toki, S. et al, Plant Physiol. 100: 1503, 1995).

For example, several techniques have already been established as methods to produce a plant transformant of rice, such as methods that regenerate plants by: introducing a gene into a protoplast using polyethylene glycol (suited for indica type rice) (Datta S. K., In Gene Transfer To Plants □Potrykus I and Spangenberg, Eds□ pp. 66–74, 1995) or by electropulse (suited for *japonica* type rice) (Toki, S. et al, Plant Physiol. 100: 1503, 1992); directly introducing a gene into a cell by the particle gun method (Christou, P. et al, Biotechnology 9: 957, 1991); or introducing a gene via the Agrobacterium (Hiei, Y. et al, Plant J. 6: 271, 1994). Such methods that are widely used in the technical field of the present invention may be preferably used in the present invention.

Once a plant transformant that has the DNA according to the present invention inserted into its genome is obtained, progenies can be obtained by sexual or asexual reproduction from that plant transformant. In addition, it is possible to obtain propagation material (for example, seeds, fruits, grafts, tubers, tubercles, stubbles, calli, and protoplasts) from the plant or a progeny or clone thereof, then using it as a source to mass-produce the plant. Plant cells induced from a plant produced in this manner are plant cells conferred with the regeneration ability.

Furthermore, the present invention provides a method of determining the presence or absence of the regeneration ability of a plant cell. In this method, first, expression of a DNA according to the present invention in a plant cell is detected. Then, the expression level of the DNA in the plant cell is compared to the expression level of the DNA in a control cell. Furthermore, if the expression level of the DNA in the plant cell is higher than the expression level in the control cell, the plant cell is judged to have a high regeneration ability.

In the present invention, there are no particular limitations on the method for detecting DNA expression, and examples of such are the differential display method, Northern hybridization method, RT-PCR method, and DNA array method. In addition, the expression of DNA can be detected by using as an index the expression of a protein encoded by the DNA.

In addition, the present invention provides a reagent used in the determination method of the present invention. One embodiment of the reagent is a reagent for determining the presence or absence of the regeneration ability of a plant cell, and comprises an oligonucleotide that comprises at least 15 nucleotides and hybridizes with the DNA according to the present invention.

The oligonucleotide specifically hybridizes to the DNA according to the present invention. Herein, "specifically hybridizes" means that under normal hybridization conditions, or preferably under stringent hybridization conditions (for example, the conditions of Sambrook et al., Molecular Cloning, Cold Spring Harbor Laboratory Press, New York, USA, 2nd edition, 1989), significant cross hybridization does not occur with DNAs encoding other proteins. If specific hybridization is possible, the oligonucleotide does not have to be completely complementary to the DNAs according to the present invention.

An oligonucleotide that comprises at least 15 nucleotides and hybridizes to the DNA according to the present invention can be used as a probe (including a plate to which the probe is immobilized) or a primer in the above mentioned determination method of the present invention. When the oligonucleotide is used as a primer, its length is normally 15 bp to 100 bp, preferably 17 bp to 30 bp. There are no particular limitations on the primer as long as at least a portion of the DNA according to the present invention can be amplified.

Furthermore, when the above-mentioned oligonucleotide is used as a probe, there are no particular limitations on the probe as long as it specifically hybridizes to the DNA according to the present invention. The probe may be a synthetic oligonucleotide, and normally has a chain length of at least 15 bp or longer.

The oligonucleotide according to the present invention can be prepared, for example, using a commercially available oligonucleotide synthesizer. A probe can be prepared as a double-stranded DNA fragment obtainable by restriction enzyme treatment, and such.

When the oligonucleotide according to the present invention is used as a probe, preferably, it is labeled as necessary. Examples of labeling methods include the method phosphorylation method that labels the 5' end of an oligonucleotide with $^{32}P$ using T4 polynucleotide kinase, and the method that incorporates a substrate nucleotide labeled with an isotope such as $^{32}P$, a fluorescent dye, or biotin, using a DNA polymerase such as Klenow enzyme, and using a random hexamer oligonucleotide, or such, as a primer (random priming method and so on).

In the reagent according to the present invention, besides the oligonucleotide which is the active ingredient, for example, sterilized water, physiological saline solution, vegetable oil, surfactant, lipid, solubilizing agent, buffer, preservatives, and such may be mixed as necessary.

A gene involved in the regeneration ability of plants was discovered by the present inventors. This gene can be used as a marker for selecting plant cells having a high regeneration ability. In addition, by introducing this gene into a plant cell, the regeneration ability can be conferred to the plant cell. Furthermore, by establishing a regeneration system for plant cells using a gene relating to regeneration ability plants, it is expected that the application of transformation techniques will become possible towards an even wider variety of plants.

Herein below, the present invention will be specifically described using examples, however, it is not to be construed as being limited thereto.

(1) Induction of Culture Cells

Upon sterilization of seeds, rice culture cells were induced according to the method by Ozawa (Ozawa, K. et al., Theor. Appl. Genet., 1989, 77, 205–211). The cells were passaged every two weeks onto an agar medium. The regeneration ability of culture cells was examined according to the method of Tsukahara et al. (Tsukahara, M. et al., Bot. Mag. Tokyo, 1992, 105, 227–233), 2 to 6 months after the induction of culture cells.

(2) Isolation of RNA

Following the protocol of Isogen (Wako), RNA was extracted from culture cells in the second week after passage.

(3) Differential Display and Cloning of DNA Fragment

Following the protocol of GeneHunter, differential display was carried out using 33P[dATP]. After excising a band in which a difference was observed, cloning was performed according to the protocol by GeneHunter.

(4) Sequencing and Isolation of Full-Length cDNA

After cloning the obtained band and proliferating the DNA, sequencing was performed following the protocol of ABI. After sequence determination, full-length cDNA was obtained following the protocol accompanying the SMART RACE cDNA Amplification Kit from Clontech. This sequence was then determined (SEQ ID NO: 1).

(5) Northern Hybridization

Probes were constructed from the 3' non-coding region of the obtained gene or from a sequence obtained by differential display, and Northern analysis was performed. Specifically, primers that have the sequences "GCGGCGT-CATCGTCAATGGC" (22nor1; SEQ ID NO: 3) and "TCATCTTCTTCCTTGCAGAT" (22nor2; SEQ ID NO: 4) were used to amplify the 3' non-coding region of the 22A gene by PCR, and this was used as a probe after purification by gel filtration. MegaPrime (Amersham) was used to produce an RI probe. After isolating RNA from culture cells using Isogen, electrophoresis was carried out using 1% formaldehyde denaturing gel following the protocol in "Short Protocols on Molecular Biology", then transferred to HybondN+ from Amersham. Then, Northern hybridization was performed using Rapid-hyb buffer from Amersham.

EXAMPLE 1

Figure 1:
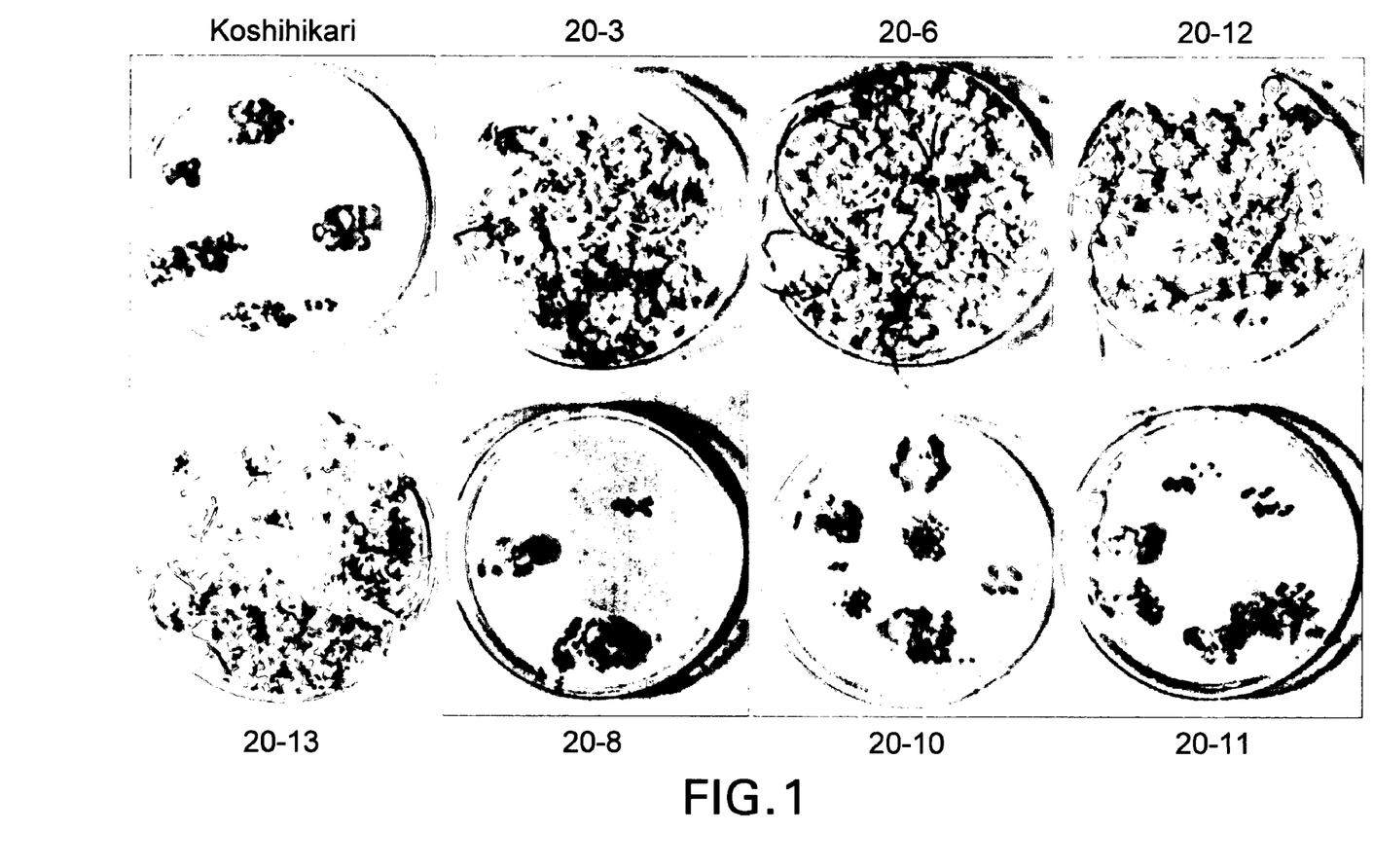
FIG. 1 depicts photographs showing the regeneration of Koshihikari and respective isogenic lines of Koshihikari.

Isogenic lines of Koshihikari and Sasanishiki introduced with the beneficial culture characteristics of Konansou (good growth of induced culture cells, and high regeneration ability) were produced. FIG. 1 shows the regeneration of Koshihikari and the isogenic line of Koshihikari. Culture cells derived from Koshihikari shows poor growth and browning, and the plants hardly regenerate. However, culture cells derived from an isogenic line introduced with the Konansou gene shows good growth, and showed a high regeneration rate of 90% or more. Differential display was carried out upon extracting RNA from culture cells in which regeneration ability was confirmed.

Figure 2:
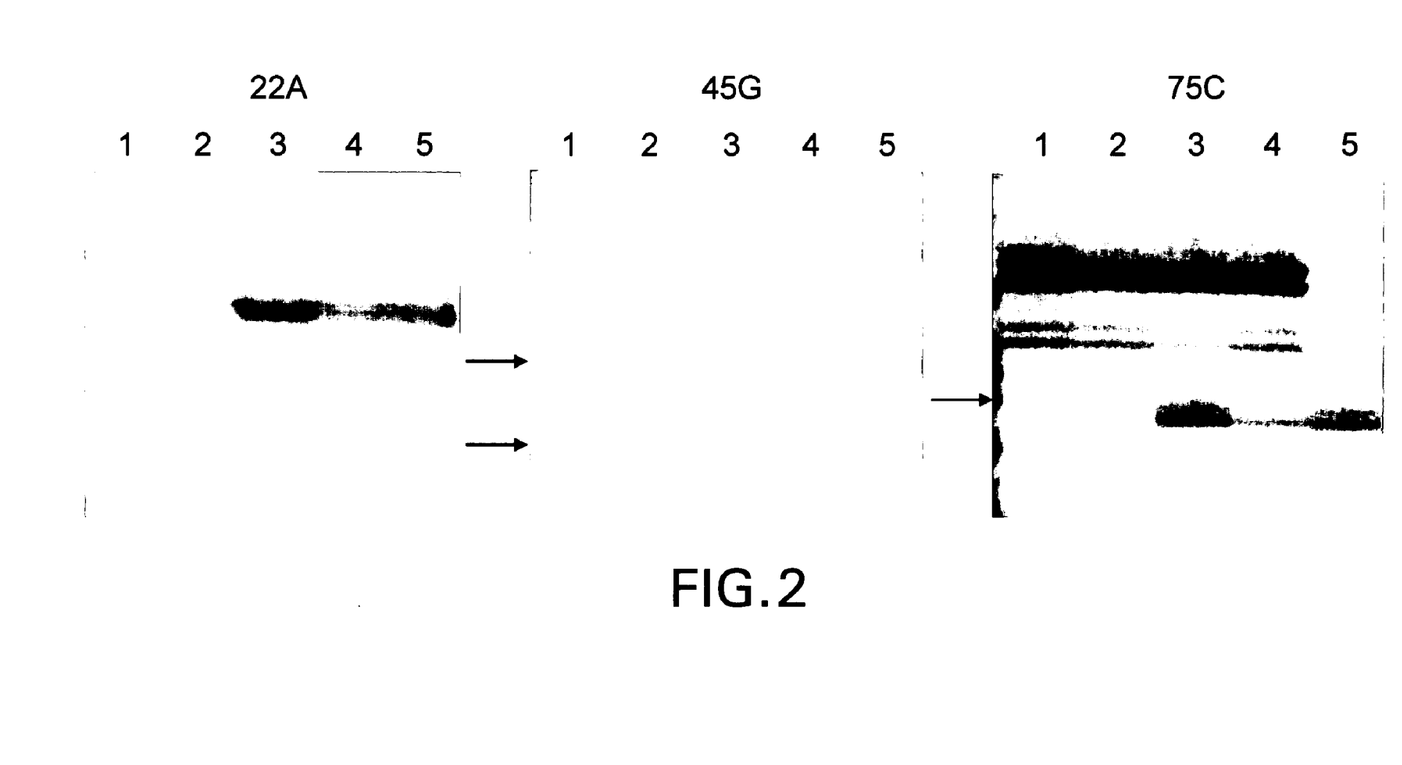
FIG. 2 depicts a photograph showing the band patterns obtained by the differential display method.

As a result, dark bands were found in Konansou and in the isogenic lines having a high regeneration ability, and extremely faint bands were found in Sasanishiki and in Koshihikari (FIG. 2). These bands were excised, cloned, and sequenced. RT-PCR was performed based on these sequences, and expression was confirmed. At the same time, among the Koshihikari B4F3 lines used for differential display, those lines in which their regeneration ability declined to the level of Koshihikari were also used simultaneously as controls. Most bands were false positives, i.e., those in which differences in expression could not be seen, and those in which expression was observed in also the control isogenic lines with low regeneration abilities. These genes were considered to be residual genes of Konansou that are not involved in the regeneration ability. Only one band was considered to be a regeneration related gene (22A).

Next, a full-length cDNA was obtained by performing 5' RACE using the DNA of SEQ ID NO: 4 as a gene specific primer. This gene (22A; SEQ ID NO: 1) (named the 22A gene) was highly homologous to Hordeum vulgare glucose and ribitol dehydrogenase homolog mRNA. The amino acid sequence of the protein encoded by the 22A gene is shown in SEQ ID NO: 2.

It has been reported that the Hordeum vulgare glucose and ribitol dehydrogenase homolog gene is expressed selectively in the late stage of embryogenesis in barley. In addition, it has been revealed that this gene metabolizes glucose. Furthermore, expression of this gene has been confirmed in a rice endosperm library and in a panicle library in the ripening stage. Additionally, expression of this gene has also been reported to occur in maize during embryogenesis. Therefore, it is strongly suggested that this gene is an embryogenesis-related gene.

EXAMPLE 2

Figure 3:
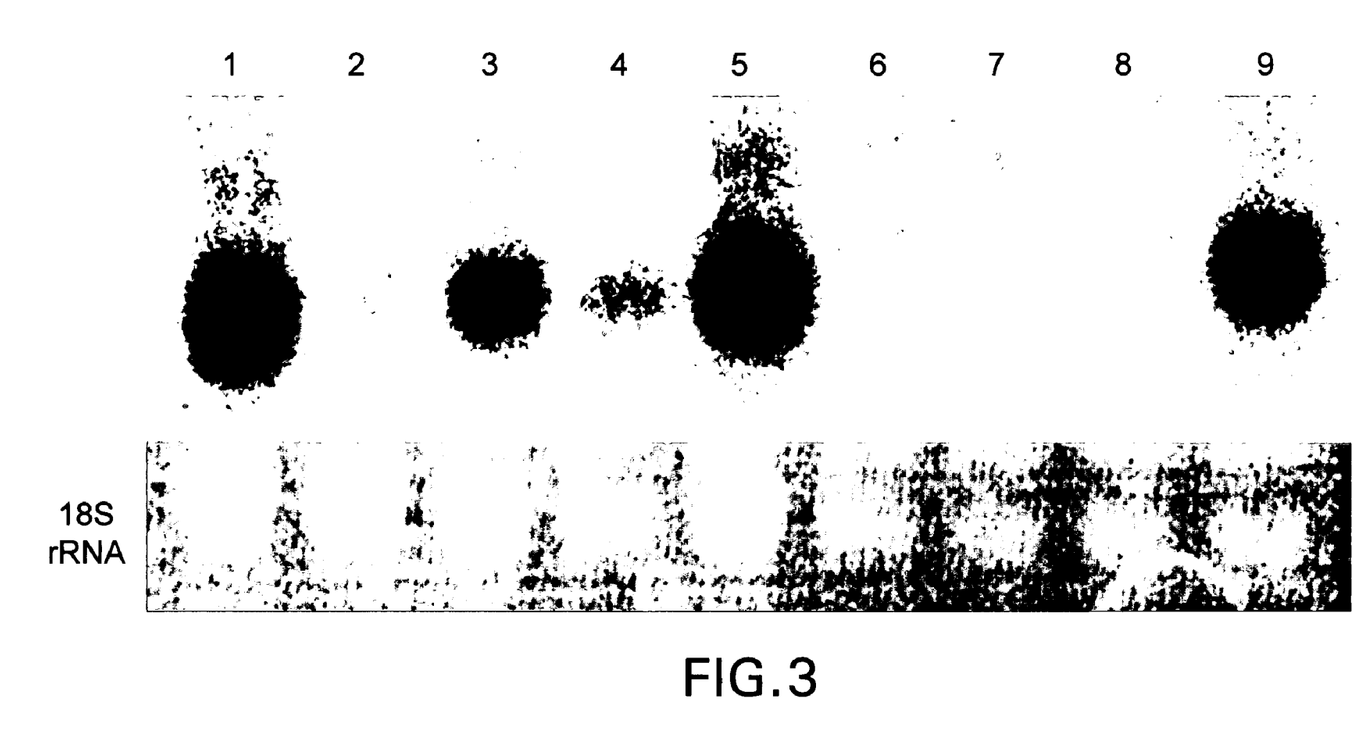
FIG. 3 depicts a photograph showing the expression pattern of the 22A gene.

Using a sequence obtained from differential display as a probe, Northern hybridization was performed (FIG. 3). Similarly to the results from differential display, 22A gene expression could not be observed in Koshihikari and Sasanishiki, but was confirmed in Konansou and in the isogenic lines having a high regeneration ability. In addition, the isogenic lines in which the regeneration ability has declined during backcrossing as in Koshihikari were also used as controls. Similarly to Koshihikari, expression of the gene could not be confirmed in these lines.

Figure 4:
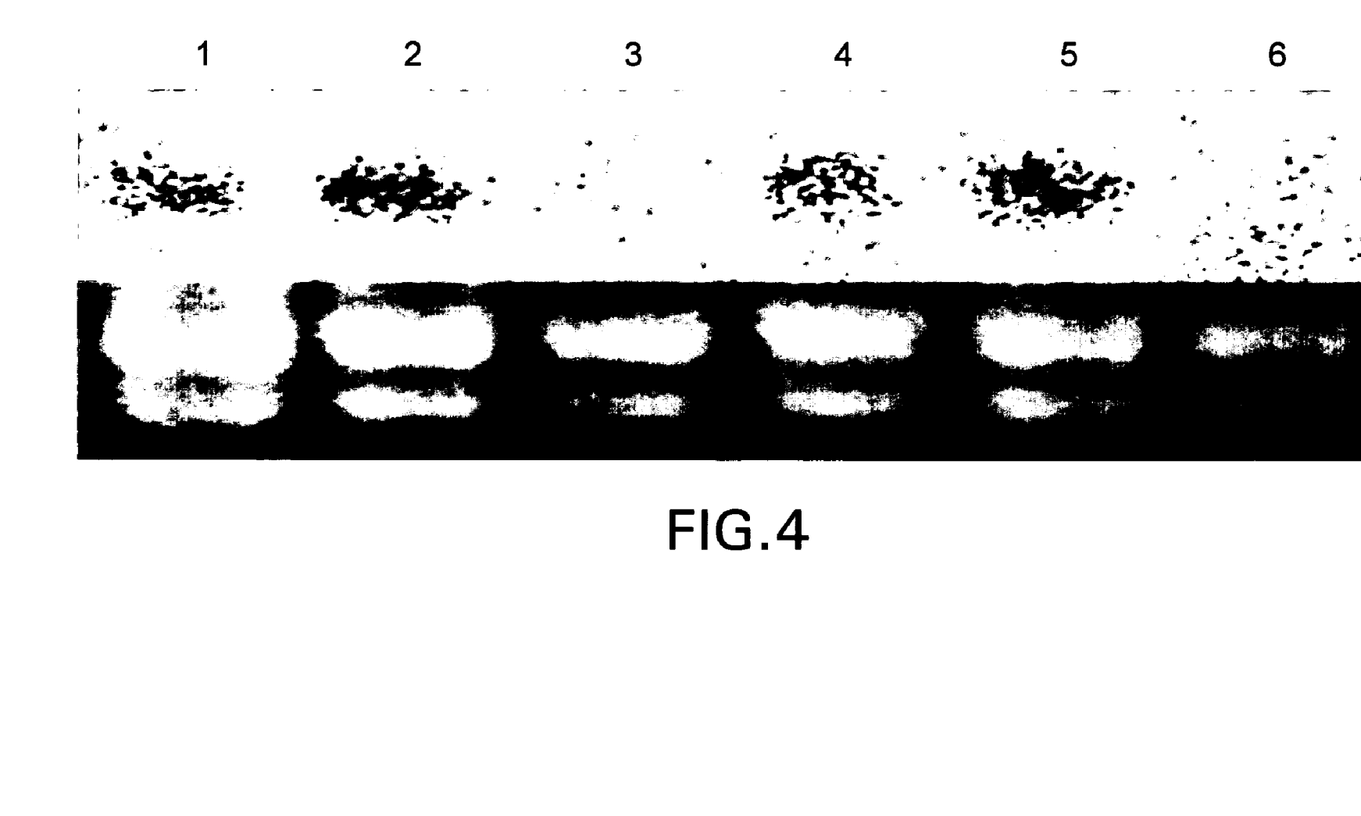
FIG. 4 depicts a photograph showing the expression pattern of the 22A gene in the respective isogenic lines.

This result alone would make one postulate that genes derived from Konansou that randomly remained as a result of backcrossing were expressed. Therefore, a B5F3 generation was obtained by backcrossing Koshihikari to Koshihikari isogenic line B4F3 having a high regeneration ability, the regeneration ability was confirmed, and then Northern hybridization was performed again using this B5F3 generation (FIG. 4). Specifically, Northern hybridization was performed using two lines of Koshihikari isogenic lines obtained by crossing two lines of B4F3 and Koshihikari. As a result, 22A gene expression was confirmed in the line having a high regeneration ability, similarly to the result of Northern hybridization obtained with B4F3. The expression of the gene could not be confirmed in the line showing a low regeneration ability.

EXAMPLE 3

Figure 5:
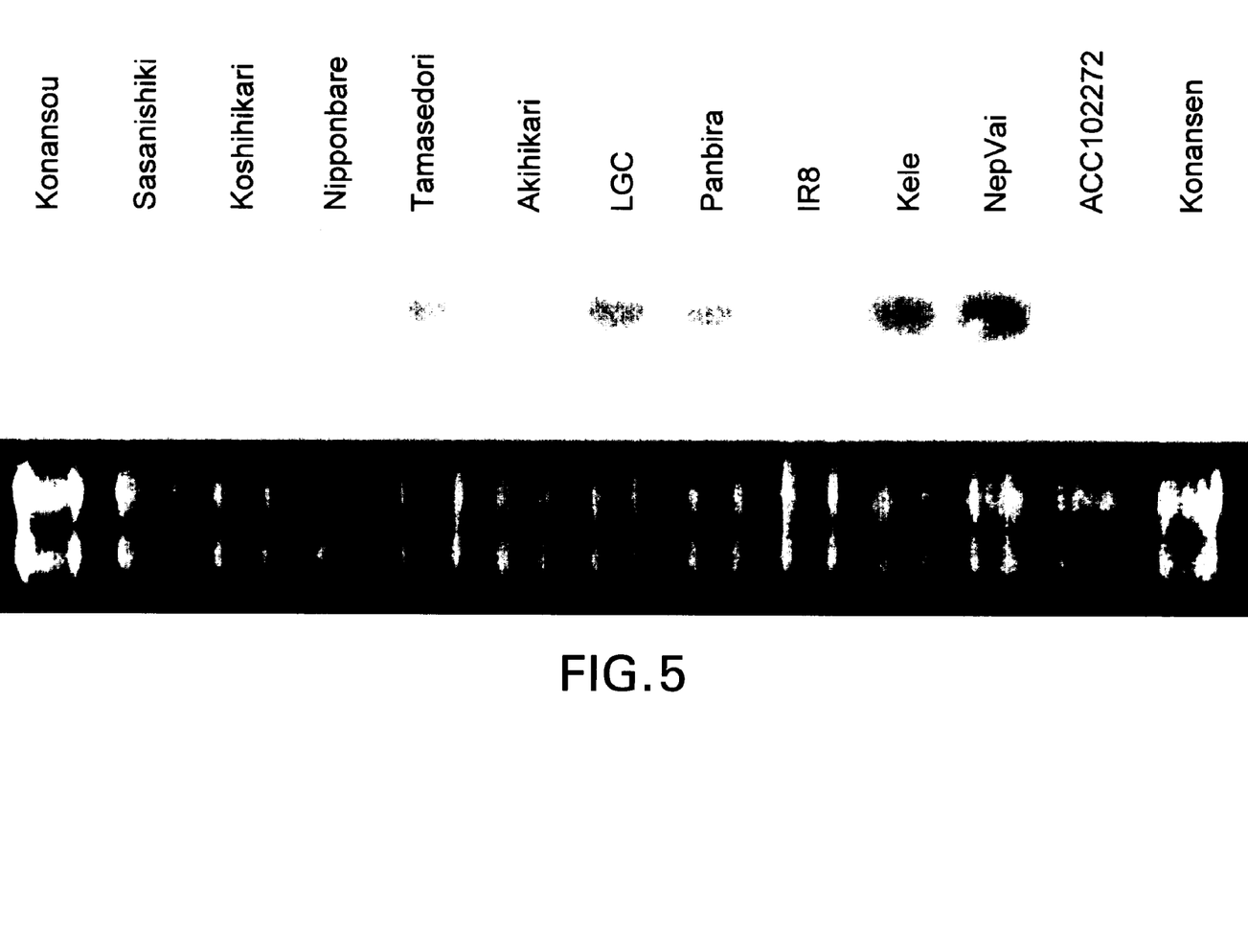
FIG. 5 depicts a photograph showing the expression pattern of the 22A gene in the respective varieties at the beginning of the culture.
Figure 6:
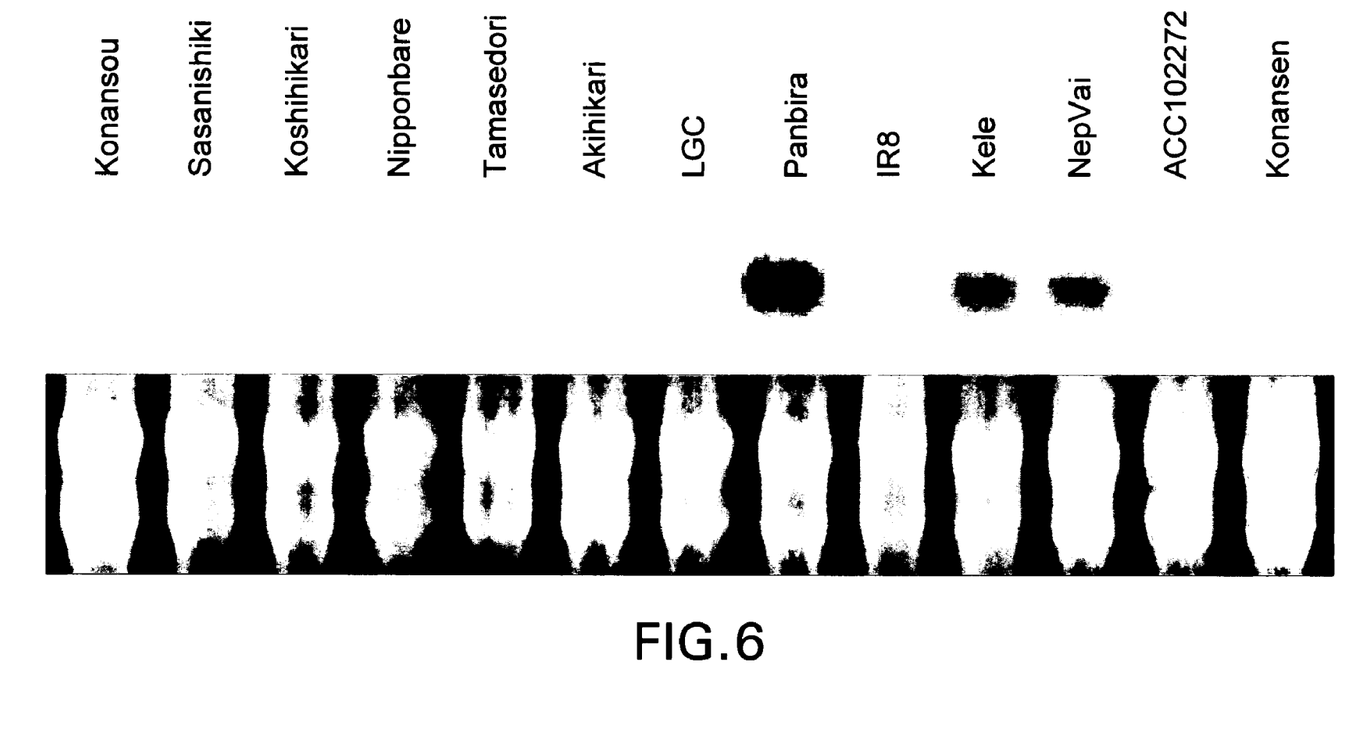
FIG. 6 depicts a photograph showing the expression pattern of the 22A gene in the respective varieties after 4 months of culture.

To verify whether there is a relationship between 22A gene expression and regeneration ability, 13 lines of rice varieties were used to examine the regeneration rate and to perform Northern hybridization (Table 1, and FIGS. 5 and 6).

TABLE 1

| Cultivar | 2 months later | 4 months later | 6 months later |
| --- | --- | --- | --- |
| Konansou | 97 | 100 | 91 |
| Sasanishiki | 100 | 45 | 35 |
| Koshihikari | 0 | 0 | 0 |
| Nipponbare | 100 | 27 | — |
| Tamasedori | 100 | 50 | — |
| Akihikari | 100 | 63 | 17 |
| LGC | 93 | 70 | |
| Panbira | 97 | 83 | 82 |
| IR8 | 7 | 0 | — |
| Kele | 100 | 87 | 82 |
| NepVai | 100 | 100 | 82 |
| ACC102272 | 73 | 93 | 0 |
| Konansen | 3 | 0 | 0 |

Figure 7:
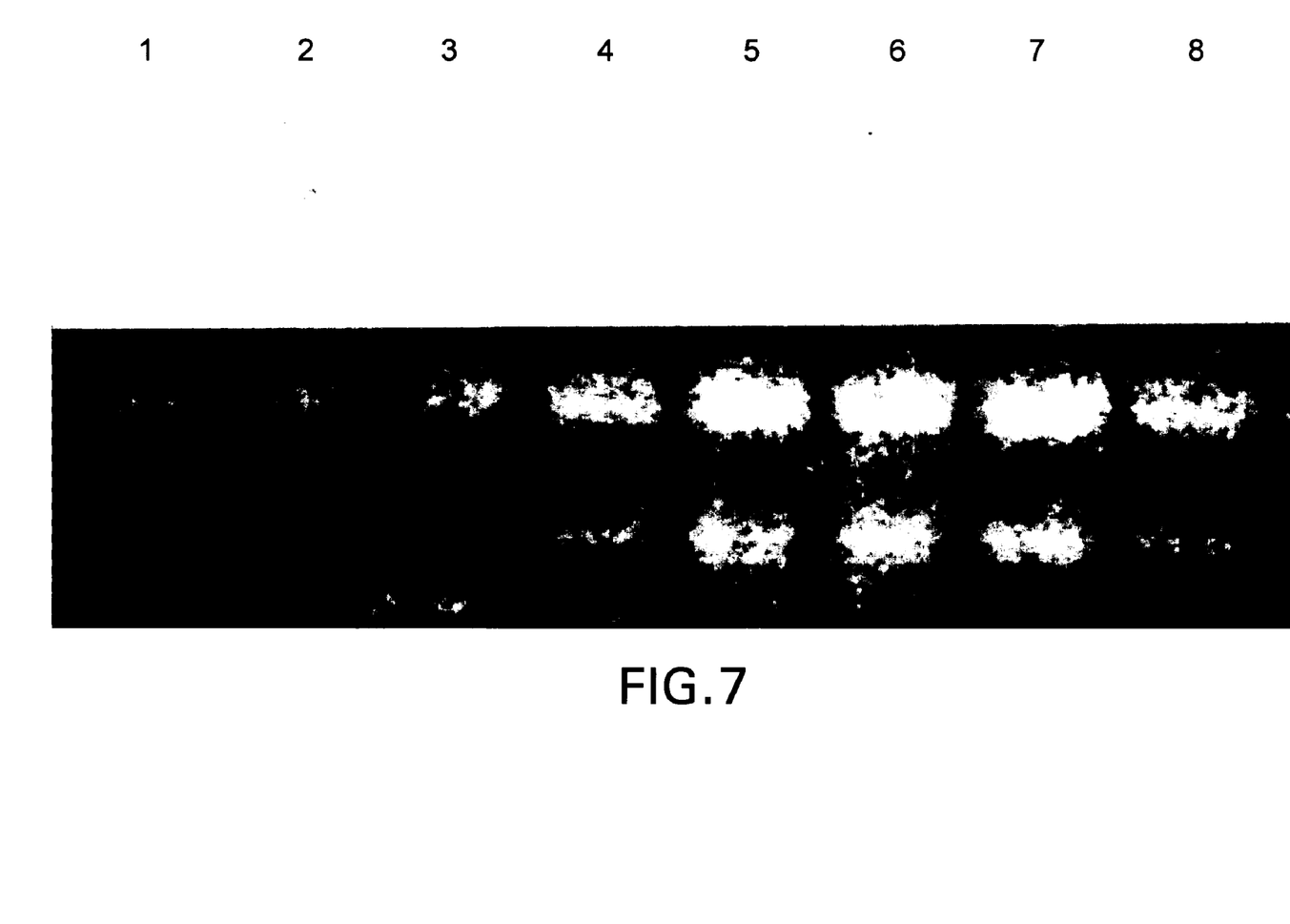
FIG. 7 depicts a photograph showing the expression pattern of the 22A gene in the respective culture cells of Nipponbare and Panbira.

A 3' non-coding region amplified by PCR was used as a probe. In Konansou, Panbira, Kele, and NepVai, in which the high regeneration ability of induced culture cells are maintained for a long period, 22A gene expression was strong in the early stage of culture cell induction, and even 4 months later. In the other varieties, expression could be hardly confirmed at the 4th month of culture. Regeneration rate also decreased. In Koshihikari, IR8, and Konansen that show poor proliferation of cells and have a low regeneration ability from the early stage of culture, expression could not be confirmed in culture cells at both the early stage of induction and in the 4th month of culture. Therefore, the regeneration ability and expression of the gene in culture cells during the early stage of culture and during the 6th month of culture was investigated in Nipponbare, in which expression was confirmed in the early stage of culture. In addition, since culture cells with a declined regeneration ability was obtained from NepVai that usually maintains a high regeneration ability for a long period, these culture cells were compared with culture cells maintaining their regeneration ability. The regeneration rate of each culture cell is indicated in Table 2, and the results of Northern hybridization are shown in FIG. 7.

TABLE 2

| Variety | Time after callus induction (months) | Regeneration rate (%) |
| --- | --- | --- |
| Nipponbare 1 | 2 | 100 |
| Nipponbare 2 | 2 | 100 |
| Nipponbare 3 | 6 | 10 |
| Nipponbare 4 | 6 | 26.7 |
| Nipponbare 5 | 6 | 33 |
| NepVai 1 | 4 | 8.3 |
| NepVai 2 | 4 | 100 |
| NepVai 3 | 4 | 93.3 |

Nipponbare had a high regeneration rate in the early stage of culture, and two lines showed a regeneration rate of 100%. However, the regeneration rate dropped to 30% or less at 6 months of culture. In addition, the NepVai 2 line showed a high regeneration ability, however NepVai 1 line had a low regeneration rate of 10% or less. The result of Northern hybridization of these 8 lines are shown in FIG. 7. 22A gene expression was confirmed in culture cells having a high regeneration ability, and expression could not be confirmed or was extremely weak in culture cells showing a low regeneration ability.

The results mentioned above strongly suggest that the 22A gene is a regeneration related gene, and that expression of the gene enables long term maintenance of the regeneration ability in culture cells. Results of expression analysis of this gene in Nipponbare culture cells in the early stage of culture and those that have been cultured for a long period, in NepVai culture cells having high regeneration ability, and in NepVai culture cells that have lost the regeneration ability, also support this view.

The regeneration ability of culture cells of Poaceae plants can rapidly decline during culture, and it has been difficult to maintain a regeneration ability for a long period. It was reported that in many Poaceae plants, a high regeneration ability can be maintained by selecting culture cells called embryogenic calli that have a high regeneration ability in each passage. It is postulated that the 22A gene may be involved in some way to form such embryonic calli. In fact, the morphology of Konansou NepVai, Kele, and Panbira culture cells is compact and white, and has a close resemblance to the reported morphology of embryonic calli.

This relationship may be elucidated through detailed investigation of 22A gene expression in Poaceae plants such as maize and wheat that are reported to form embryonic calli. Culture cells having a high regeneration ability can be selected by using the expression of this gene as a marker. Until now, the selection and maintenance of Poaceae plant culture cells having a high regeneration ability was only possible by visual observation, however, by investigating the 22A gene expression, the selection of cells can be accomplished with ease.

EXAMPLE 4

Figure 8:
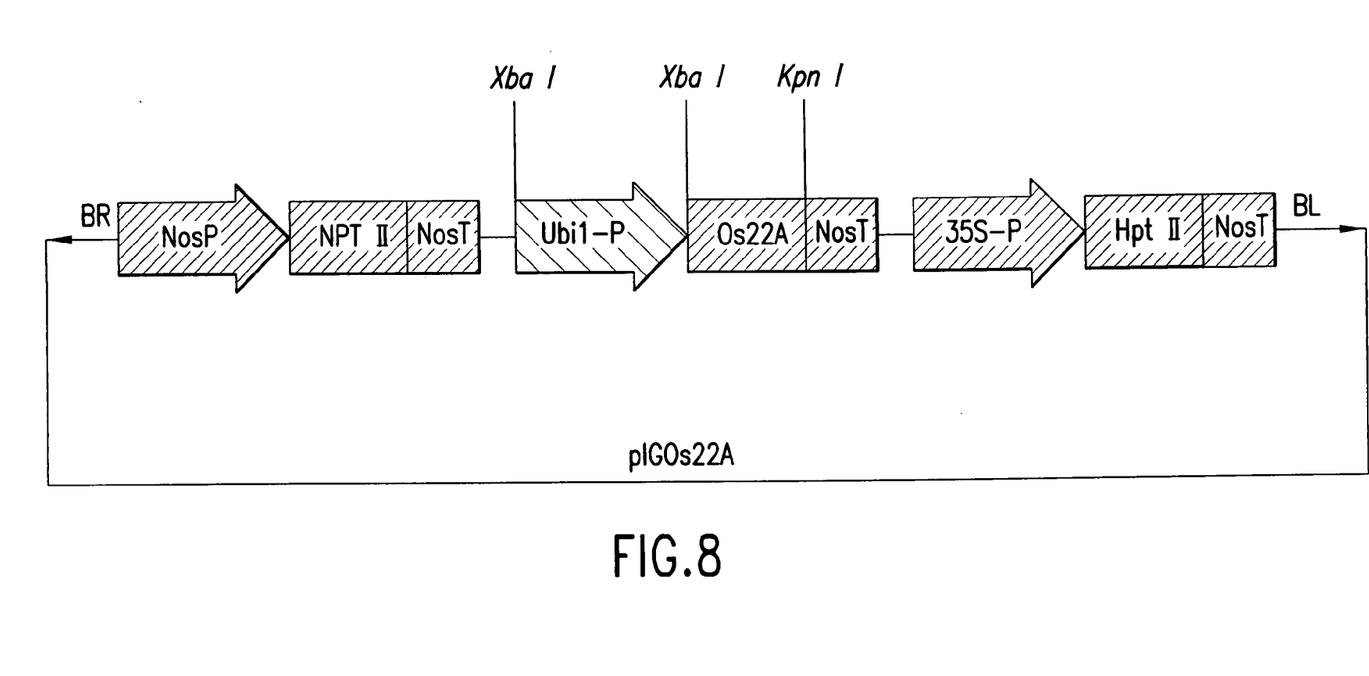
FIG. 8 depicts the construction of a binary vector comprising Os22A cDNA for rice transformation. NosP, nopaline synthase promoter; NPT II, neomycin phosphotransferase II; NosT, 3' signal of the nopaline synthase gene; ubi1-P, maize ubiquitin 1 gene promoter; 35S-P, cauliflower mosaic virus 35S promoter; HptII, hygromycin B phosphotransferase; BR, right border; BL, left border. Arrows indicate the direction of transcription.
Figure 9:
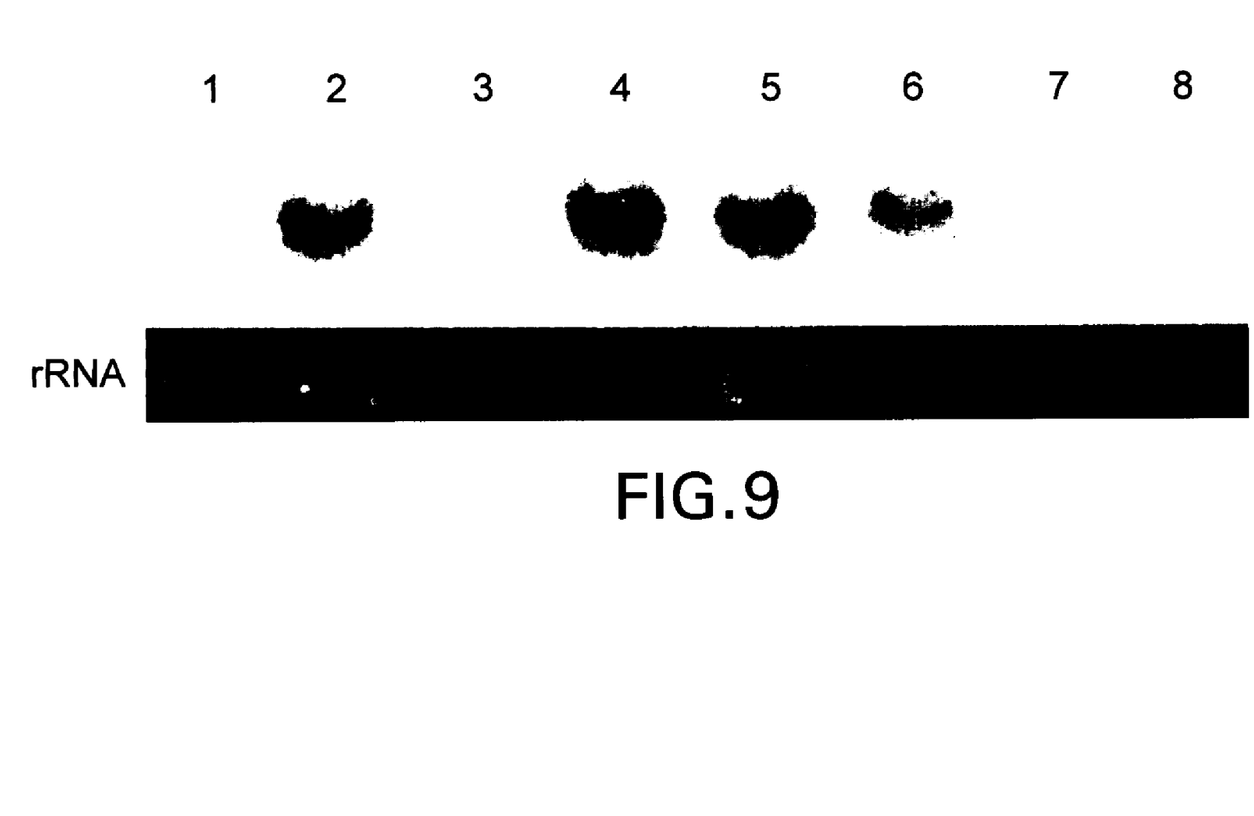
FIG. 9 depicts a photograph showing the expression pattern of Os22A in transformed calli initiated from Koshihikari as analyzed by northern blot analysis. Lane 1: Koshihikari; lanes 2–8: Transformed calli of Koshihikari. Total RNA (15 µg/lane) from calli was subjected to Northern hybridization analysis.

The 22A gene was introduced into the rice variety Koshihikari by the Agrobacterium method upon constructing an expression vector driven by a ubiquitin (Ubi-1) promoter, which is a promoter that induces strong expression in monocotyledonous plants (FIG. 8). After selecting hygromycin resistant calli, mRNA was extracted from each callus, Northern hybridization was performed, and expression of the inserted gene was examined using the resistant calli (FIG. 9).

Figure 10:
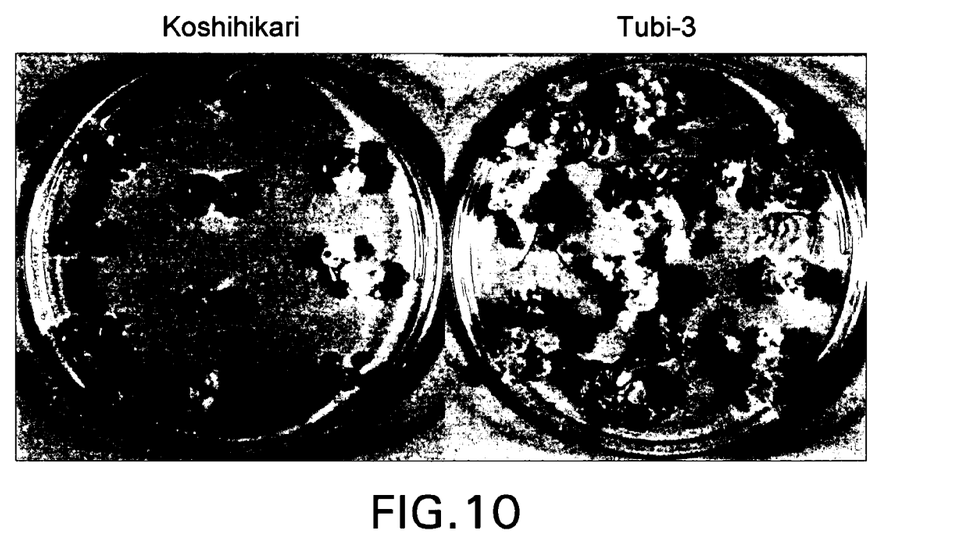
FIG. 10 depicts a photograph showing the regeneration from calli initiated Koshihikari and transformed calli of Koshihikari. Transformed calli, that were screened by hygromycin selection and subcultured in N6 medium supplemented with 2,4-dichlorophenoxy acetic acid (2,4-D; 2 mg/L), proline (10 mM), casein hydrolysate (300 mg/L), sucrose (30 g/L) and gelrite (4 g/L) at three weekly intervals, were transferred to the regeneration medium. Tubi-3: Transformed calli initiated from Koshihikari.

Next, the transformed calli were planted onto a regeneration medium, and their regeneration rates were determined (FIG. 10, Table 3).

TABLE 3

| Cell line | % of the regeneration |
|---|---|
| Koshihikari 1 | 5.8 ± 5.2 |
| Koshihikari 2 | 3.3 ± 5.8 |
| Koshihikari 3 | 3.8 ± 4.0 |
| Tubi-2 | 99 ± 1.1 |
| Tubi-3 | 100 ± 0 |
| Tubi-6 | 98 ± 3.8 |
| Tubi-13 | 100 ± 0 |

The values represent an average from three independent experiments. ±:the standard deviation.

As a control callus, a callus that has not been transformed was used. In addition, regeneration rate was calculated from "number of regenerated calli/number of planted calli". As a result, transformed calli clearly showed a high regeneration ratio compared to Koshihikari used as a control, and plant regeneration occurred from almost all calli. From the results mentioned above, the Os22A gene was considered to have an extremely important function in induction of calli showing a high regeneration ability.

What is claimed is:

1. An isolated DNA encoding a protein that enhances the regeneration ability of a plant, wherein the DNA is selected from the group consisting of:
   (a) a DNA encoding a protein, comprising the amino acid sequence of SEQ ID NO: 2; and
   (b) a DNA comprising the coding region of the nucleotide sequence of SEQ ID NO: 1.

2. A vector into which the DNA according to claim 1 has been introduced.

3. A transformed plant cell harboring the DNA according to claim 1.

4. A plant transformant comprising the transformed plant cell according to claim 3.

5. A plant transformant which is a progeny or clone of the plant transformant according to claim 4, wherein said progeny or clone harbors said DNA, wherein said DNA is selected from the group consisting of:
   (a) a DNA encoding a protein, comprising the amino acid sequence of SEQ ID NO: 2; and
   (b) a DNA comprising the coding region of the nucleotide sequence of SEQ ID NO: 1.

6. A propagation material of the plant transformant according to claim 4, wherein said propagation material harbors said DNA, wherein said DNA is selected from the group consisting of:
   (a) a DNA encoding a protein, comprising the amino acid sequence of SEQ ID NO: 2; and (b) a DNA comprising the coding region of the nucleotide sequence of SEQ ID NO: 1.

7. A propagation material of the plant transformant according to claim 5, wherein said propagation material harbors said DNA, wherein said DNA is selected from the group consisting of:
   (a) a DNA encoding a protein, comprising the amino acid sequence of SEQ ID NO: 2; and
   (b) a DNA comprising the coding region of the nucleotide sequence of SEQ ID NO: 1.

8. A transformed plant cell harboring the vector according to claim 2.

9. A plant transformant comprising the transformed plant cell according to claim 8.

10. A plant transformant which is a progeny or clone of the plant transformant according to claim 9, wherein the transformant harbors said DNA, wherein said DNA is selected from the group consisting of:

(a) a DNA encoding a protein, comprising the amino acid sequence of SEQ ID NO: 2; and (B) a DNA comprising the coding region of the nucleotide sequence of SEQ ID NO: 1.

11. A propagation material of the plant transformant according to claim 9, wherein the propagation material harbors said DNA, wherein said DNA is selected from the group consisting of:

(a) a DNA encoding a protein, comprising the amino acid sequence of SEQ ID No: 2; and (b) a DNA comprising the coding region of the nucleotide sequence of SEQ ID NO: 1.

12. A propagation material of the plant transformant according to claim 10, wherein the propagation material harbors said DNA, wherein said DNA is selected from the group consisting of:

(a) a DNA encoding a protein, comprising the amino acid sequence of SEQ ID NO: 2; and (b) a DNA comprising the coding region of the nucleotide sequence of SEQ ID NO: 1.

13. A method for producing the plant transformant according to claim 4, wherein the method comprises the following steps of:

(a) introducing said DNA into a plant cell, wherein said DNA is selected from the group consisting of:

(i) a DNA encoding a protein, comprising the amino acid sequence of SEQ ID NO: 2; and (ii) a DNA comprising the coding region of the nucleotide sequence of SEQ ID NO: 1.; and (b) regenerating a plant from said plant cell.

14. A method for producing the plant transformant according to claim 9, wherein the method comprises the following steps of:

(a) introducing said vector into a plant cell; and (b) regenerating a plant from said plant cell.

\* \* \* \* \*